US00PP16932P2

(12) United States Plant Patent
Westhoff

(10) Patent No.: US PP16,932 P2
(45) Date of Patent: Aug. 1, 2006

(54) ***CALIBRACHOA* PLANT NAMED 'WESCARASP'**

(50) Latin Name: ***Calibrachoa* sp.**
Varietal Denomination: Wescarasp

(75) Inventor: Heinrich Westhoff, Südlohn (DE)

(73) Assignee: J. & H. Westhoff Interpel, Südlohn (DE)

( * ) Notice: Subject to any disclaimer, the term of this patent is extended or adjusted under 35 U.S.C. 154(b) by 0 days.

(21) Appl. No.: 11/146,211

(22) Filed: Jun. 6, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Calibrachoa* plant named 'Wescarasp', characterized by its semi-upright and vigorous growth habit; freely branching habit; short internodes; dense and bushy appearance; relatively small-sized leaves; medium-sized flowers; and numerous red purple-colored flowers with dark purple-colored venation and circumorbital ring.

1 Drawing Sheet

Botanical designation: *Calibrachoa* sp.
Cultivar denomination: 'Wescarasp'.

BACKGROUND OF THE INVENTION

The present Invention relates to a new and distinct cultivar of *Calibrachoa* plant, botanically known as *Calibrachoa* sp., and hereinafter referred to by the cultivar name 'Wescarasp'.

The new *Calibrachoa* is a product of a planned breeding program conducted by the Inventor in Südlohn, Germany. The objective of the breeding program is to develop new vigorous *Calibrachoa* cultivars with attractive and unique flower coloration.

The new *Calibrachoa* originated from a cross-pollination made by the Inventor in 2000 of a proprietary selection of *Calibrachoa* identified as code number 00P108, not patented, as the female, or seed, parent with a proprietary selection of *Calibrachoa* identified as code number 00P192, not patented, as the male, or pollen, parent. The new *Calibrachoa* was discovered and selected by the Inventor in a controlled environment in Südlohn, Germany as a single plant within the resulting progeny from the cross-pollination.

Asexual reproduction of the new cultivar by terminal cuttings at Südlohn, Germany since 2001, has shown that the unique features of this new *Calibrachoa* are stable and reproduced true to type in successive generations.

SUMMARY OF THE INVENTION

Plants of the cultivar Wescarasp have not been observed under all possible environmental conditions. The phenotype may vary with variations in environment such as temperature and light intensity without, however, any variance in genotype.

The following traits have been repeatedly observed and are determined to be the unique characteristics of 'Wescarasp'. These characteristics in combination distinguish 'Wescarasp' as a new and distinct cultivar of *Calibrachoa:*

1. Semi-upright and vigorous growth habit.
2. Freely branching habit; short internodes; dense and bushy appearance.
3. Relatively small-sized leaves.
4. Medium-sized flowers.
5. Numerous red purple-colored flowers with dark purple-colored venation and circumorbital ring.

Plants of the cultivar Wescarasp can be compared to plants of the female parent selection. In side-by-side comparisons conducted in Südlohn, Germany, plants of the new *Calibrachoa* differed from plants of the female parent selection in the following characteristics:

1. Plants of the new *Calibrachoa* had darker green-colored leaves than plants of the female parent selection.
2. Plants of the new *Calibrachoa* and the female parent selection differed in flower color as plants of the female parent selection had lighter pink-colored flowers.

Plants of the cultivar Wescarasp can be compared to plants of the male parent selection. In side-by-side comparisons conducted in Südlohn, Germany, plants of the new *Calibrachoa* differed from plants of the male parent selection in the following characteristics:

1. Plants of the new *Calibrachoa* were more upright than and not as cascading as plants of the male parent selection.
2. Plants of the new *Calibrachoa* had shorter internodes than plants of the male parent selection.
3. Plants of the new *Calibrachoa* and the male parent selection differed in flower color as plants of the male parent selection had blue violet-colored flowers.

Plants of the new *Calibrachoa* can also be compared to plants of the *Calibrachoa* cultivar Wescadarkblue, disclosed in U.S. Plant Pat. No. 15,119. In side-by-side comparisons conducted in Südlohn, Germany, plants of the new *Calibrachoa* differed from plants of the cultivar Wescadarkblue in the following characteristics:

1. Plants of the new *Calibrachoa* were more compact and more upright than plants of the cultivar Wescadarkblue.

2. Plants of the new *Calibrachoa* had broader leaves than plants of the cultivar Wescadarkblue.
3. Plants of the new *Calibrachoa* had shorter peduncles than plants of the cultivar Wescadarkblue.
4. Plants of the new *Calibrachoa* and the cultivar Wescadarkblue differed in flower color.

Plants of the new *Calibrachoa* can also be compared to plants of the *Calibrachoa* cultivar Wescaplum, disclosed in U.S. Plant Pat. No. 15,069. In side-by-side comparisons conducted in Südlohn, Germany, plants of the new *Calibrachoa* differed from plants of the cultivar Wescaplum in the following characteristics:

1. Plants of the new *Calibrachoa* were more upright than and not as cascading as plants of the cultivar Wescaplum.
2. Plants of the new *Calibrachoa* had smaller and darker green-colored leaves than plants of the cultivar Wescaplum.
3. Plants of the new *Calibrachoa* had lighter purple-colored flowers than plants of the cultivar Wescaplum.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the bottom of the sheet comprises a side perspective view of typical flowering plants of 'Wescarasp' grown in a container.

The photograph at the top of the sheet is a close-up view of typical flowers of 'Wescarasp'.

DETAILED BOTANICAL DESCRIPTION

Plants used in the aforementioned photographs and for the following description were grown under conditions which closely approximate commercial production conditions during the spring and summer in a glass-covered greenhouse in Südlohn, Germany. Plants were about 20 weeks from planting rooted cuttings and grown in containers. During the production of the plants, the day temperatures ranged from 20 to 25° C., night temperatures ranged from 16 to 18° C. and light levels ranged from 3,000 to 50,000 lux.

In the following description, color references are made to The Royal Horticultural Society Colour Chart, 2001 Edition, except where general terms of ordinary dictionary significance are used.

Botanical classification: *Calibrachoa* sp. cultivar Wescarasp.

Parentage:

*Female parent.*—Proprietary selection of *Calbrachoa* sp. identified as 00P108, not patented.

*Male parent.*—Proprietary selection of *Calbrachoa* sp. identified as 00P192, not patented.

Propagation:

*Type cutting.*—Terminal vegetative cuttings.

*Time to initiate roots.*—About 18 to 20 days at 20° C.

*Time to develop roots.*—About 20 to 28 days at 20° C.

*Root description.*—Numerous, fine, fibrous, and well-branched.

Plant description:

*Form.*—Annual flowering plant; semi-upright; uniform, rounded appearance, plants eventually become spherical in overall shape. Freely branching with lateral branches forming at every node. Vigorous growth habit.

*Usage.*—Appropriate for hanging baskets, window boxes and patio containers.

*Plant height (from soil level to top of plant plane).*—About 15.6 cm.

*Plant length (from soil level to lateral branches apices).*—About 50 cm.

*Stem description.*—Main branches, length: About 45 cm. Main branches, diameter: About 2.3 mm. Lateral branches, length: About 16 cm. Lateral branches, diameter: About 1 mm. Internode length: About 9.5 mm. Texture: Pubescent. Strength: Strong, wiry. Color: 144B tinted with 174A.

*Foliage description.*—Arrangement: Alternate, simple; sessile. Length: About 2.6 cm. Width: About 1.1 cm. Shape: Oblanceolate to elliptic. Apex: Obtuse. Base: Attenuate. Margin: Entire. Aspect: Mostly flat. Texture, upper and lower surfaces: Pubescent; leathery. Venation: Pinnate. Color: Developing foliage, upper surface: 137A. Developing foliage, lower surface: 146A. Fully expanded foliage, upper surface: 147A; midvein, 147B; lateral veins, similar to lamina. Fully expanded foliage, lower surface: 147B; midvein, 147C; lateral veins, similar to lamina.

Flower description:

*Flower type and habit.*—Medium-sized flowers; flowers face upright or outward; single, axillary. Flowers not persistent. Freely flowering with flowers forming at every axil.

*Natural flowering season.*—Spring until frost in the autumn; flowering continuous.

*Flower longevity on the plant.*—About one week.

*Flower size.*—Diameter: About 3 cm. Depth (height): About 2 cm. Tube length: About 1.4 cm. Throat diameter, distal end: About 7 mm. Tube diameter, proximal end: About 2 mm.

*Flower buds.*—Length: About 1.9 cm. Diameter: About 4 mm. Shape: Oblong. Color: Towards the base, 144D; mid-section, N79A; towards the apex, N79B to N79C.

*Corolla.*—Arrangement/appearance: Single whorl of five petals, fused into flared trumpet. Petal length from throat: About 1.2 cm. Petal width: About 1.4 cm. Petal shape: Roughly spatulate with a rounded apex. Petal margin: Entire. Petal texture, upper and lower surfaces: Smooth, glabrous; satiny. Color: Petal, when opening, upper and lower surfaces: 64A. Petal, fully opened, upper surface: 64A to 64B; color becoming closer to N79C with development; circumorbital ring, N79A; venation, N79A to 79C. Petal, fully opened, lower surface: 70A to 70B; venation, N79A to N79B. Flower throat (inside): 2A; venation, N79A. Flower tube (outside): 144C; venation, N79A.

*Sepals.*—Arrangement/appearance: Single whorl of five sepals, star-shaped. Length: About 1.3 cm. Width: About 3.2 mm. Shape: Lanceolate. Apex: Acute. Margin: Entire. Texture, upper and lower surfaces: Pubescent. Color, upper and lower surfaces: 146A.

*Peduncles.*—Length: About 9.3 mm. Width: About 1 mm. Strength: Flexible, wiry. Texture: Slightly pubescent. Color: 144A.

*Reproductive organs.*—Stamens: Quantity per flower: Five. Anther shape: Four-parted, ovate. Anther length: About 1.2 mm. Anther diameter: About 1.1 mm. Filament length: About 5.5 mm. Filament color: 145C. Anther color: 6C. Pollen amount: Moderate. Pollen color: 6C. Pistils: Quantity per flower: One. Pistil length: About 8 mm. Stigma shape: Ovate. Stigma color: 144B. Style length: About 6 mm. Style color: 145C overlain with 177C. Ovary color: 144B.

*Seed/fruit.*—Seed and fruit production has not been observed.

Disease/pest resistance: Plants of the new *Calibrachoa* have not been noted to be resistant to pathogens and pests common to *Calibrachoa*.

Temperature tolerance: Plants of the new *Calibrachoa* have been observed to be tolerant to temperatures ranging from 2 to 30° C.

It is claimed:

1. A new and distinct cultivar of *Calibrachoa* plant named 'Wescarasp', as illustrated and described.

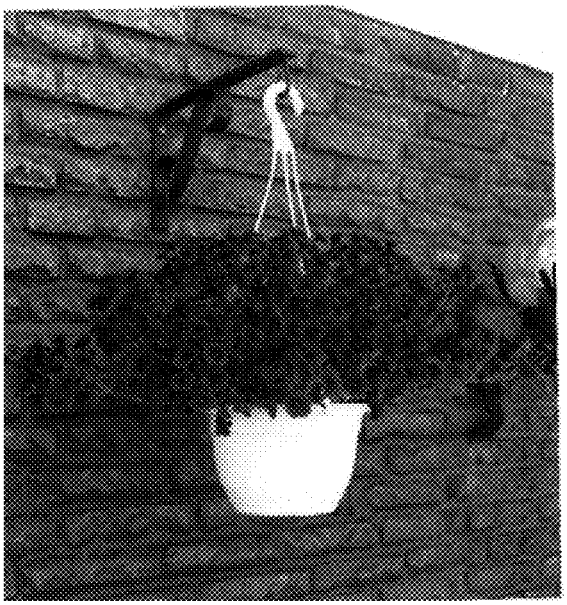
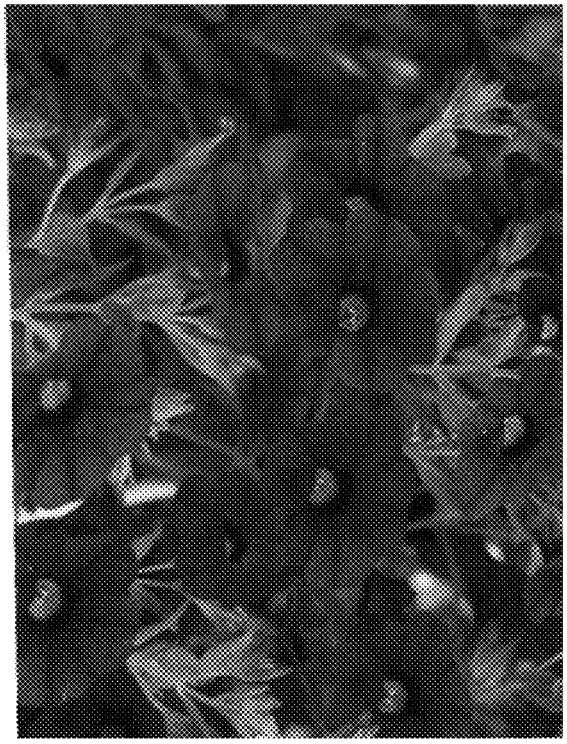

* * * * *